United States Patent [19]

Albrecht et al.

[11] 3,954,981

[45] May 4, 1976

[54] TRIAZOLOCYCLOALKYLHYDROTHIADIAZINE DERIVATIVES

[75] Inventors: William L. Albrecht; Winton D. Jones, both of Cincinnati, Ohio

[73] Assignee: Richardson-Merrell Inc., Wilton, Conn.

[22] Filed: Apr. 28, 1975

[21] Appl. No.: 571,940

[52] U.S. Cl. .............................. 424/246; 260/243 R; 260/240 J; 260/243 R;240 J
[51] Int. Cl.² ............... C07D 285/20; C07D 285/22
[58] Field of Search .................................... 424/246

[56] References Cited
OTHER PUBLICATIONS

George et al., J. Med. Chem., Vol. 14, pp. 335–338 (1971).

*Primary Examiner*—John M. Ford
*Attorney, Agent, or Firm*—William J. Stein; Eugene O. Retter; George W. Rauchfuss, Jr.

[57] ABSTRACT

Novel triazolocycloalkylhydrothiadiazines and their preparation, which are useful as antisecretory agents, central nervous system stimulants, and central nervous system depressants, are disclosed.

11 Claims, No Drawings

TRIAZOLOCYCLOALKYLHYDROTHIADIAZINE DERIVATIVES

SUMMARY OF THE INVENTION

This invention relates to new triazolocycloalkylhydrothiadiazines, their method of preparation, compositions thereof, and their usefulness as pharmaceutical agents. More particularly, the novel compounds of this invention are derivatives of triazolocycloalkylhydrothiadiazines, which can be represented by the following structural formula

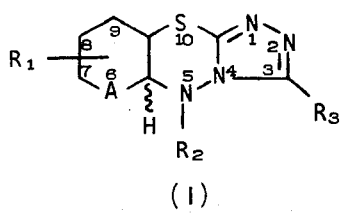

(I)

wherein $R_1$ is selected from the group consisting of hydrogen and lower alkyl having from 1 to 4 carbon atoms, inclusively; $R_2$ is selected from the group consisting of hydrogen, acetyl, N-carbamoylacetic acid (ethyl ester), cinnamoyl and anilinocarbonyl; $R_3$ is selected from the group consisting of hydrogen and alkyl having from 1 to 15 carbon atoms inclusively, trifluoromethyl, cycloalkyl having from 3 to 6 carbon atoms inclusively, phenyl, alkoxyalkyl having from 2 to 8 carbon atoms, inclusively; and phenoxyalkyl having from 7 to 10 carbon atoms inclusively; A is a sigma bond or the radical $-(CH_2)_n-$ in which n is a whole integer of from 1 to 7; and the pharmaceutically acceptable acid addition salts thereof.

In general, the triazolocycloalkylhydrothiadiazine derivatives in which $R_2$ is hydrogen are prepared by reducing the corresponding triazolocycloalkylthiadiazines in solution with either sodium borohydride or lithium aluminum hydride. The triazolocycloalkylthiadiazines, in turn, are obtained by condensing a 4-amino-4H-1,2,4-triazole-3-thiol with an α-haloalicyclic ketone. This complete reaction sequence can be schematically represented as follows:

In order to achieve an antisecretory effect, or an effect upon the central nervous system, an effective amount of a compound of formula (I) is internally administered to an animal to be treated. Various pharmaceutical compositions including convenient dosage unit forms are also described herein.

BACKGROUND OF THE INVENTION

The treatment of conditions associated with gastric hyperacidity is almost as ancient as recorded history. Peptic and gastroduodenal ulcers have been variously treated both in the past and at present by means of bland diets, the exclusion of certain foods which are mechanically or chemically irritating and foods which do not stimulate gastric secretion.

Additionally, neutralizing drugs, which buffer or neutralize gastric contents; antispasmodics which reduce excessive gastroduodenal motor activity; sedatives which are used to induce general relaxation in ulcer patients; enzyme inhibitors which inhibit pepsin the proteolytic enzyme secreted by gastric cells; nutritional supplements; mucosal protective agents and histamine antagonists have all been employed. Each of these drugs has its inadequacies as can be seen from the variety of drugs employed.

The most striking feature in the treatment of ulcers, has been a concern with gastric acidity. The rationale of gastric secretory depressant therapy lies in the hope that an agent can be found which will diminish or inhibit the process of hydrochloric acid formation in gastric cells without concomitant damage to these cells or harm to the host. The compounds of the present invention are antisecretory agents having a specific activity against gastric secretion in animals. Thus, they are useful for reducing or inhibiting gastric acid secretion and for the treatment of peptic ulceration. The term peptic ulceration is used in its broad sense, as is conventional in the art, to include both gastric ulceration and duodenal ulceration.

Additionally, certain of these compounds are physiologically useful in view of their systemic action upon the central nervous system of vertebrates. Certain of the compounds disclosed herein act as central nervous

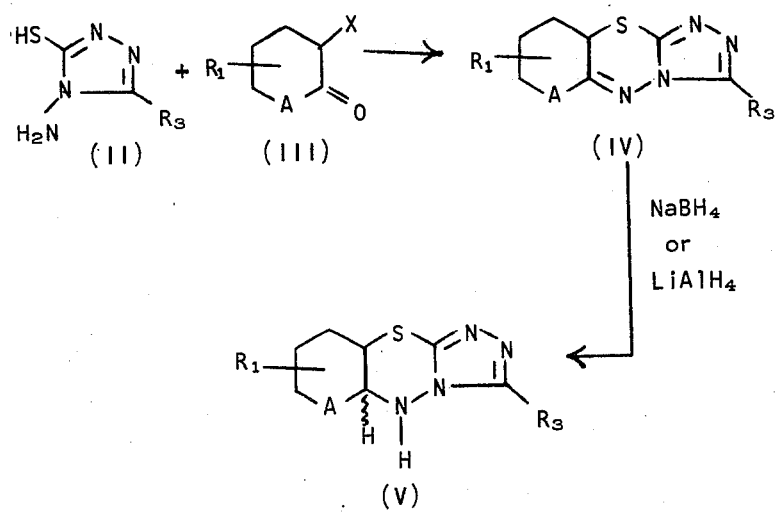

In the above reaction sequence, the symbols $R_1$, $R_3$ and A have the values previously assigned, and X is halogen selected from the group consisting of chlorine, bromine and iodine.

system depressants and can be administered either orally or parenterally to mammals for the relief of excessive anxiety and tension. Other compounds act as stimulants upon the central nervous system and are therefore useful as mood elevators and psychic energizers in the treatment of depressed mental health conditions.

The closest art known to applicants discloses a series of 5-alkyl-4-amino-s-triazole-3-thiols stated to have analgetic and antiinflammatory activities, George et al., J. Med. Chem. 14, 335 (1971). Disclosed therein are four compounds which contain a triazolothiadiazine nuclear moiety. The prior art compounds, however, lack the cycloalkyl portion of the nucleus necessary for the compounds of the present invention. Moreover, the prior art compounds possess completely different pharmacological properties from those properties described for the compounds herein.

DETAILED DESCRIPTION OF THE INVENTION

As can be seen from general formula (I) and its description above, the compounds of the present invention include derivatives of triazolocycloalkylhydrothiadiazine, which are substituted in the cycloalkyl, the thiadiazine and the triazole portions of the ring nucleus. The cycloalkyl ring can be unsubstituted or may be mono-substituted with a lower alkyl group as indicated by the symbol $R_1$. The term "lower alkyl" refers to a univalent, aliphatic, carbon side chain comprising such radicals as methyl, ethyl, propyl, isopropyl, butyl, isobutyl or tertiary-butyl.

The thiadiazine ring can be unsubstituted as indicated when the symbol $R_2$ is hydrogen. Additionally, the thiadiazine ring is substituted at the 5-position with four specific groups, namely, the acetyl, N-carbamoylacetic acid (ethyl ester), cinnamoyl and anilinocarbonyl groups.

Lastly, the triazole ring may remain unsubstituted or it can be mono-substituted at the 3-position with a variety of substituents as indicated by the symbol $R_3$. Thus, $R_3$ can represent an alkyl group. However, in this instance, the alkyl group contains from 1 to 15 carbon atoms, inclusively. In addition to the specific lower alkyl groups previously mentioned, the symbol $R_3$ also includes such groups as amyl, hexyl, heptyl, octyl, nonyl, decyl, undecyl, dodecyl, tridecyl, tetradecyl and pentadecyl. Additionally, the various branched and positional isomers are included so long as the alkyl group is univalent and does not exceed a total of 15 carbon atoms in length.

The symbol $R_3$ can also represent a univalent cycloalkyl group having from 3 to 6 carbon atoms. Illustrative of such groups are the cyclopropyl, cyclobutyl, cyclopentyl and cyclohexyl radicals.

Certain univalent alkyl ethers are also represented by the symbol $R_3$. These ether moieties can be aliphatic in nature, as for example when $R_3$ is alkoxyalkyl. The term "alkoxyalkyl" is limited to alkyl ethers having a carbon content of from 2 to 8 carbon atoms. Illustrative members of this group include: methoxymethyl, methoxyisopropyl, methoxyheptyl, ethoxyethyl, ethoxyhexyl, propoxypropyl, propoxyisobutyl, isobutoxymethyl, amyloxymethyl, hexyloxyethyl and isoheptyloxymethyl. The ether moiety can also be aromatic in nature as represented by the expression phenoxyalkyl wherein the carbon content of the combined phenoxyalkyl group ranges from 7 to 10 carbon atoms. Illustrative members of this group include: phenoxymethyl, phenoxyethyl, phenoxypropyl, phenoxyisopropyl, phenoxybutyl, phenoxyisobutyl and phenoxy-t-butyl. Specific univalent radicals also encompassed by the symbol $R_3$ include the trifluoromethyl and the phenyl radicals.

The symbol A represents either a sigma bond or the radical $-(CH_2)_n-$ wherein n is a whole integer of from 1 to 7 in order to encompass the various cycloalkyl moieties of the triazolocycloalkylhydrothiadiazine nucleus. The expression "sigma bond" refers to the ordinary single bond linkage between two adjacent carbon atoms resulting from the overlap of their corresponding orbitals. Thus, where A represents a sigma bond, the subgeneric class of triazolocyclopentylhydrothiadiazines is delineated. Where A represents the radical $-(CH_2)_n-$ and $n$ is the integer 1, the corresponding class of triazolocyclohexylhydrothiadiazines is delineated. Where $n$ is the integer 2, the class of triazolocycloheptylhydrothiadiazines is delineated, etc. The various cycloalkyl moieties of the triazolocycloalkylhydrothiadiazine nucleus encompassed by the present invention include the cyclopentyl, cyclohexyl, cycloheptyl, cyclooctyl, cyclononyl, cyclodecyl, cycloundecyl and the cyclododecyl moieties.

A preferred subgeneric class of compounds is obtained when the symbol $R_2$ is hydrogen. These compounds are directly prepared by the reduction of the corresponding triazolocycloalkylthiadiazines are described below.

Another preferred subgeneric class of compounds is obtained when the symbol A is the radical $-(CH_2)_n-$ and n is the integer 1. Such compounds are designated as triazolocyclohexylhydrothiadiazines and are readily prepared from known 2-halocyclohexanones.

Still another preferred subgeneric class of compounds is obtained when the symbol A is the radical $-(CH_2)_n-$ and n is the integer 2. Such compounds are designated as triazolocycloheptylhydrothiadiazines and possess excellent central nervous system stimulant and depressant activities.

Illustrative of the specific base compounds encompassed by formula (I) above and which are being claimed herein are the compounds:

5-acetyl-5,5a,6,7,8,8a-hexanhydro-6-methyl-3-propyl-s-triazolo[3,4-b][1,3,4]cyclopentathiadiazine, 5,5a,6,7,8,8a-hexahydro-3-pentadecyl-8-propyl-s-triazolo[3,4-b][1,3,4]cyclopentathiadiazine, 5-cinnamoyl-3-cyclopropyl-7-ethyl-5,5a,6,7,8,8a-hexahydro-s-triazolo[3,4-b][1,3,4]cyclopentathiadiazine, 5,5a,6,7,8,8a-hexahydro-6-isobutyl-3-methoxyheptyl-s-triazolo[3,4-b]1,3,4]cyclopentathiadiazine, 5-anilinocarbonyl-3-decyl-5a,6,7,8,9,9a-hexahydro-6-isopropyl- 5H-s-triazolo[3,4-b][1,3,4]cyclohexathiadiazine, 9-t-butyl-3-trifluoromethyl-5a,6,7,8,9,9a-hexahydro-5H-s-triazolo[3,4-b][1,3,4]cyclohexathiadiazine, 5-[N-carbamoylacetic acid (ethyl ester)]-5a,6,7,8,9,9a-hexahydro-3-methoxymethyl-8-propyl-5H-s-triazolo[3,4-b]-[1,3,4]cyclohexathiadiazine, 5a,6,7,8,9,9a-hexahydro-7-methyl-3-phenoxypropyl-5H-s-triazolo[3,4-b][1,3,4]cyclohexathiadiazine, 5-acetyl-5,5a,6,7,8,9,10,10a-octahydro-3-octyl-6-propyl-s-triazolo[3,4-b][1,3,4]cycloheptathiadiazine, 3-cyclopropyl-9-ethyl-5,5a,6,7,8,9,10,10a-octahydro-s-triazolo[3,4-b][1,3,4]cycloheptathiadiazine, 5,5a,6,7,8,9,10,10,a-octahydro-3-isoamyloxyethyl-7-isobutyl-s-triazolo[3,4-b][1,3,4]cycloheptathiadiazine, 5-cinnamoyl-5,5a,6,7,8,9,10,10a-octahydro-10-methyl-3-phenyl-s-triazolo[3,4-b][1,3,4]cycloheptathiadiazine, 5-anilinocarbonyl-6-butyl-5a,6,7,8,9,10,11,11a-octahydro-3-isobutyl-5H-s-triazolo[3,4-b][1,3,4]cyclooctathiadiazine, 3-ethyl-5a,6,7,8,9,10,11,11a-octahydro-10-methyl-5H-s-triazolo[3,4-b][1,3,4]cyclooctathiadiazine, 5-N-carbamoylacetic acid (ethyl ester)]-11-ethyl-3-trifluoromethyl-5a,6,7,8,9,10,11,11a-octahydro-5H-s-triazolo-[3,4-b][1,3,4]cyclooctathiadiazine, 5a,6,7,8,9,10,11,11a-octahydro-8-isopropyl-3-phenoxy-isobutyl-5-H-s-triazolo[3,4-b][1,3,4]cyclooctathiadiazine, 5-acetyl-3-butyl-5a,6,7,8,9,10,11,12,13,13a-decahydro-13-methyl-5H-s-triazolo[3,4-b][1,3,4]cyclodecathiadiazine, 3-cyclopentyl-5a,6,7,8,9,10,11,12,13,13a-decahydro-8-isopropyl-5-H-s-triazolo[3,4-b][1,3,4]cyclodecathiadiazine, 5-cinnamoyl-11-ethyl-5a,6,7,8,9,10,11,12,13,13a-decahydro-3-nonyl-5H-s-triazolo[3,4-b][1,3,4]cyclodecathiadiazine, 6-butyl-3-hexyloxymethyl-5a,6,7,8,9,10,11,12,13,13a-decahydro-5H-s-triazolo[3,4-b][1,3,4]cyclodecathiadiazine, 5a,6,7,8,9,10,11,12,13,14,15,15a-dodecahydro-3-isododecyl-15-methyl-5H-s-triazolo[3,4-b][1,3,4]cyclododecathiadiazine, 5-anilinocarbonyl-3-cyclohexyl-5a,6,7,8,9,10,11,12,13,14,15,15a-dodecahydro-6-isobutyl-5-H-s-triazolo[3,4-b][1,3,4]-cyclododecathiadiazine, 5-[N-carbamoylacetic acid (ethyl ester)]-12-ethyl-5a,6,7,8,9,10,11,12,13,14,15,15a-dodecahydro-3-phenyl-5H-s-triazolo[3,4-b][1,3,4]cyclododecathiadiazine, and 5a,6,7,8,9,10,11,12,13,14,15,15a-dodecahydro-3-phenoxymethyl-9-propyl-5H-s-triazolo[3,4-b][1,3,4]cyclododecathiadiazine.

The expression "pharmaceutically acceptable acid addition salts" refers to any non-toxic inorganic or organic acid addition salts of the base compounds represented by formula (I) above. Illustrative inorganic acids which form suitable salts include hydrochloric, hydrobromic, sulfuric and phosphoric acid and acid metal salts such as sodium monohydrogen orthophosphate and potassium hydrogen sulfate, Illustrative organic acids which form suitable salts include the mono, di and tricarboxylic acids. Such acids include, for example, acetic, glycolic, lactic, pyruvic, malonic, succinic, glutaric, fumaric, malic, tartaric, citric, ascorbic, maleic, benzoic, p-hydroxybenzoic, phenylacetic, cinnamic, salicyclic, 2-phenoxybenzoic and sulfonic acids such as methane sulfonic acid and 2-hydroxyethane sulfonic acid. Due to the fact that the triazolocycloalkylhydrothiadiazines are relatively weak organic bases, the salts formed by the addition of strong inorganic mineral acids are more readily isolated and represent the preferred salts of this invention. In addition to salt formation, the free base compounds of this invention may exist in either a hydrated or a substantially anhydrous form. Generally speaking, the acid addition salts of these compounds are crystalline materials which are soluble in water and various hydrophilic organic solvents and in comparison to their free base forms, generally demonstrate a higher melting point and an increased chemical stability.

The starting materials used in the preparation of the compounds described herein are prepared via standard or known specific procedures. Thus, the 4-amino-4H-1,2,4-triazole-3-thiols of formula (II) above can be prepared by the reaction of thiocarbohydrazide (VI) with an appropriate carboxylic acid or substituted carboxylic acid (VII) in accordance with the following reaction scheme:

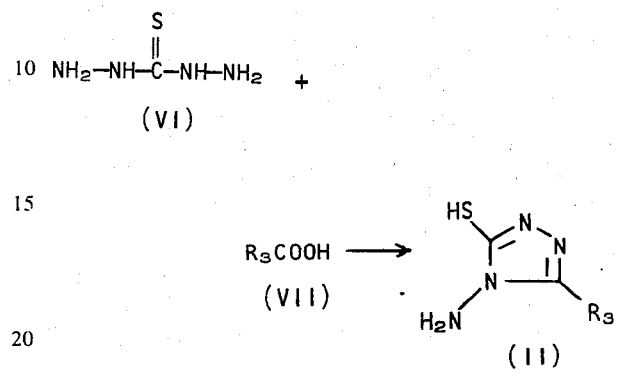

Where $R_3$ is phenyl, the procedure of Example 2 is employed.

In general, these reactants are heated together at temperatures ranging from 100° to about 160° C. in the presence or absence of a solvent for a period of about 1 to 12 hours. The resulting triazole can then be recovered using standard methods known to those skilled in the art.

The 2-halocycloalkanones of formula (III) above are either commercially available or can be reaily prepared via the halogenation of their corresponding cycloalkanones. Suitable halogenating agents include bromine, chlorine, cupric bromide and sulfuryl chloride. The 2-iodocycloalkanones can be prepared via a halogen interchange involving the treatment of the corresponding 2-chloro or 2-bromocycloalkanones with sodium or potassium iodide in an acetone solution.

The triazolocycloalkylthiadiazines (IV) are readily obtained by condensing the 4-amino-4H-1,2,4-triazole-3-thiols (II) with the 2-halocycloalkanones (III) described above. Where either or both of the reactants are liquid in nature, condensation can be achieved by simple admixture and heating. Alternatively, the reaction can take place in a suitable inert solvent. Suitable non-reactive solvents include the lower alkanols, chloroform, dioxane, diethyl ether, tetrahydrofuran, pentane, hexane, heptane, benzene and toluene. The solvents of choice include the lower alkanols having from 1 to 6 carbon atoms, such as methanol, ethanol, isopropanol, amyl alcohol and n-hexanol, with ethanol representing the preferred solvent.

The temperature at which condensation takes place varies from about room temperature to about 150° C. Preferably, the condensation is conducted at temperatures which range from about 60° to about 100° C. in order to obtain maximum yields. As a matter of convenience, the reflux temperature of the reaction mixture is generally employed.

The reaction time is partly a function of the temperature employed, and partly a function of the degree of stearic hindrance encountered. Additionally, the nature of the various substituents may necessitate adjusting the reaction period. A reaction time of about 1 hour to about 12 hours is generally sufficient for condensation to occur. Preferably, the reaction is conducted for about 1 to 2 hours in order to minimize any thermal degradation that may occur.

The triazolocycloalkylthiadiazines (IV) are generally isolated by concentrating the reaction mixture in vacuo to form an oily or solid residue. This residue can then be dissolved in an organic solvent such as chloroform or methylene chloride, and extracted with an aqueous alkaline solution, such as a 5 or 10% sodium hydroxide solution, in order to remove impurities and unreacted starting materials. The organic extracts are washed, dried and concentrated to obtain the desired product as a crude material. These crude products can be readily purified in a standard manner by recrystallization from ordinary solvent mixtures including methanol, ethanol, ethyl acetate, methylene chloride, hexane and pentane.

The triazolocycloalkylhydrothiadiazines of the present invention, wherein $R_2$ is hydrogen (V), are prepared by reducing the triazolocycloalkylthiadiazines described above (IV). In general, reduction is accomplished in a suitable solvent using either sodium borohydride or lithium aluminum hydride as a reducing agent at temperatures which range from about −20° C. to about 100° C., for periods of time which range anywhere from about 30 minutes to about 24 hours. A variety of solvents can be suitably employed, as for example, tetrahydrofuran, ether, dioxane, methanol, ethanol, isopropanol and water. When aqueous or methanolic solutions of sodium borohydride are employed, a base such as sodium hydroxide is utilized in order to minimize the rate at which the sodium borohydride reagent decomposes. Preferably, the reduction is accomplished by dissolving the triazolocycloalkylthiadiazines (IV) in tetrahydrofuran or methanol and adding solid sodium borohydride in small increments with continued stirring. Ice bath temperatures can be initially employed with suitable stirring, whereupon the temperature of the reaction mixture is gradually increased and maintained at its reflux temperature until complete.

Upon completion of the reaction the triazolocycloalkylhydrothiadiazines (V) can be isolated and purified either as the free base compounds or as their hydrohalide salts. The reaction mixture can be concentrated in vacuo to form an oily or solid residue which is then dissolved in a dilute solution of hydrochloric acid, filtered, neutralized and redissolved in an organic solvent such as chloroform or methylene chloride. The organic solvent is removed in vacuo and the residue containing the desired product can be recrystallized from such solvents as ether, tetrahydrofuran, hexane, methanol, ethanol, ethyl acetate, chloroform or mixtures and aqueous mixtures thereof. Saturation of a solvent such as tetrahydrofuran or methylene chloride with dry hydrogen chloride, for example, results in the desired triazolocycloalkylhydrothiadiazines (V) being obtained as their hydrochloride salts.

The triazolocycloalkylhydrothiadiazines (V) can also be substituted at the 5-position of the thiadiazine portion of the nucleus with either an acetyl, n-carbamoylacetic acid (ethyl ester), cinnamoyl or anilinocarbonyl group.

The 5-acetyl derivatives are prepared by reacting acetyl chloride or acetic anhydride and sodium acetate with the particular triazolocycloalkylhydrothiadiazine (V) to be acylated. The resulting mixture is heated to its reflux temperature for a period ranging from 2 to 24 hours. The resulting acetamides are readily isolated and purified via standard procedures.

The 5-[N-carbamoylacetic acid (ethyl ester)] derivatives are prepared by condensing carbethoxymethylisocyanate with a triazolocycloalkylhydrothiadiazine (V) as described above. Condensation is readily effected by stirring the triazolocycloalkylhydrothiadiazine directly into liquid carbethoxymethylisocyanate at elevated temperatures and isolating the desired product therefrom.

The 5-cinnamoyl derivatives are prepared by treating the desired triazolocycloalkylhydrothiadiazine (V) with cinnamoyl chloride at elevated temperatures in the presence of pyridine in a suitable solvent, such as benzene. In general, dilution of the reaction mixture with a solvent such as hexane results in the precipitation of the desired 5-cinnamoyl derivative which can then be separated and purified, as for example, by recrystallization.

The 5-anilinocarbonyl derivatives are prepared by treating a triazolocycloalkylhydrothiadiazine of formula (V) above with an excess of phenylisocyanate. In general, the reaction is conducted in a suitable solvent, such as benzene, at elevated or reflux temperatures. The desired product which precipitates during the reaction can be further purified by recrystallization from a suitable solvent, as for example, methanol.

The compounds of the present invention and their nontoxic, pharmacologically acceptable acid addition salts, have useful pharmacodynamic properties. More particularly, the compounds of this invention exhibit effective stomach ulcerinhibiting and stomach juice secretion-inhibiting properties in mammals including, for example, such species as: mice, rats, guinea pigs, gerbils, hamsters, rabbits, ferrets, dogs, cats, cows, horses and humans. The inhibiting action of the compounds claimed herein upon the rate of secretion of the stomach juice and the amount of secreted total hydrochloric acid is ascertained in laboratory rats by means of a modification of the standard test method of Shay et al., Gastroenterology 5, 43-61 (1945). In this regard, the following triazolocycloheptylhydrothiadiazines are of particular interest, namely, 3-ethyl-5,5a,6,7,8,9,10,-10a-octahydro-s-triazolo[3,4-b][1,3,4]cycloheptathiadiazine; 5,5a,6,7,8,9,10,10a-octahydro-3-methyl-s-triazolo[3,4-b][1,3,4]cycloheptathiadiazine; 5,5a,6,7,8,9,10,10a-octahydro-3-phenoxymethyl-s-triazolo[3,4-b][1,3,4]cycloheptathiadiazine, and 5-acetyl-3-ethyl-5,5a,6,7,8,9,10,10a-octahydro-s-triazolo[3,4-b][1,3,4]cycloheptathiadiazine.

The central nervous system depressant properties for these compounds are characterized as sedative depressants by their effect on pernicious preening in mice according to the procedure of Kandel et al., Fed. Proc., 19, 21 (1960). Of particular interest are the compounds 5a,6,7,8,9,9a-hexahydro-5H-s-triazolo[3,4,-b][1,3,4]cyclohexathiadiazine, and 5,5a,6,7,8,9,10,-10a-octahydro-3-methyl-s-triazolo[3,4-b]-[1,3,4]cycloheptathiadiazine.

Certain of these compounds also selectively remit reserpine-induced extrapyramidal motor deficits or catalepsy induced in experiment animals. Thus, the instant compounds are useful as antidepressants, antiparkinson agents and are useful for the treatment of catalepsy and Parkinsonian-like effects resulting from the administration of neuroleptic agents to mammals in need thereof, illustrative of such compounds are 5a,6,7,8,9,9a-hexahydro-3-methoxymethyl-5H-s-triazolo[3,4-b][1,3,4]cyclohexathiadiazine; 3-ethyl-5a,6,7,8,9,9a-hexahydro-5H-s-triazolo[3,4-b]-

[1,3,4]cyclohexathiadiazine; 3-ethyl-5,5a,6,7,8,9,10,-10a-octahydro-s-triazolo[3,4-b][1,3,4]cyclohepta-thiadiazine; 3-ethyl-5a,6,7,8,9,10,11,11a-octahydro-5H-s-triazolo[3,4-b]-[1,3,4]cyclooctathiadiazine; and 5-acetyl-3-ethyl-5,5a,6,7, 8,9,10,10a-octahydro-s-triazolo[3,4-b][1,3,4]cycloheptathiadiazine.

The basic compounds of this invention also form thiocyanic acid addition salts which, when condensed with formaldehyde, form resinous materials useful as pickling inhibitors in accordance with U.S. Pat. Nos. 2,425,320 and 2,606,155. Further, the fluosilicic acid addition salts of said basic compounds are useful as moth-proofing agents in accordance with U.S. Pat. Nos. 1,915,334 and 2,075,359.

For pharmaceutical purposes, the compounds of this invention can be administered to warm-blooded animals perorally or parenterally as active ingredients in customary dosage unit compositions. These compositions consist essentially of a dosage unit form containing the active ingredient and an inert pharmaceutical carrier. Dosage unit forms contemplated by the present invention include tablets, coated pills, capsules, dragees, lozenges, wafers, powders, elixirs, clear liquid solutions, suspensions, emulsions, syrups, and parenteral compositions such as intramuscular, intravenous or intradermal preparations. The quantity of active ingredient administered in such dosage forms can vary over a wide range depending upon the mode of administration, the size and weight of the particular mammal to be treated and whether the nature of the treatment is to be prophylactic or therapeutic in nature. In general, dosage unit forms contain from about 5 mg. to about 2.0 g. of the active ingredient, administered anywhere from 1 to 4 times daily. A therapeutically effective amount of the active ingredient comprises from about 1 to about 200 mg/kg of body weight per day.

The excipients used in the preparation of the pharmaceutical compositions may be either organic or inorganic, solid or liquid in nature. Suitable solid excipients include gelatin, lactose, starches, magnesium stearate and petrolatum. Suitable liquid excipients include water and alcohols such as ethanol, benzyl alcohol and polyethylene glycols either with or without the addition of a suitable surfactant. In general, the preferred liquid excipients, particularly useful for injectable preparations, include water, saline solution, dextrose and glycol solutions, such as aqueous propylene glycol or an aqueous solution of polyethylene glycol. Liquid preparations to be used as sterile injectable solutions will ordinarily contain from about 0.5 to about 25% by weight, and preferably from about 1 to about 10% by weight, of the active ingredient in solution.

A preferred method of administration for the compounds of the present invention is peroral, either in a solid dosage form such as a tablet or capsule, or in a liquid form such as an oral elixir, suspension, emulsion or syrup. Tablets containing the active ingredient are prepared by mixing an inert diluent such as lactose in the presence of a disintegrating agent, e.g., maize starch and lubricating agents such as magnesium stearate. Such tablets can, if desired, be provided with enteric coatings using methods known to those skilled in the art, as for example, the use of cellulose acetate phthalate. Similarly, either hard or soft shelled gelatin capsules, can contain a compound of formula (I), with or without additional excipients and can be prepared by conventional means. Furthermore, if desired, such capsules can be provided with enteric coatings known to the art. Tablets and capsules can conveniently contain about 25–500 mg. of the active ingredient. Other less preferred compositions for oral administration include aqueous solutions, suspensions, emulsions, or syrups. Ordinarily, the active ingredient comprises from about 0.5 to about 10% by weight in such compositions. The pharmaceutical carrier is generally aqueous in nature, as for example, aromatic water, a sugar-based syrup or a pharmaceutical mucilage. For insoluble compounds, suspending agents can also be added as well as agents to control viscosity, as for example, magnesium aluminum silicate or carboxymethylcellulose. Buffers, preservatives, emulsifying agents and other excipients known to the art can also be added.

For parenteral administration such as intramuscular, intravenous or subcutaneous administration, the proportion of active ingredient ranges from about 0.05 to about 20% by weight and preferably from about 0.1% to about 10% by weight of the liquid composition. In order to minimize or eliminate irritation at the site of injection, such compositions may contain a non-ionic surfactant having a hydrophile-lipophile balance (HLB) of about 12 to about 17. The quantity of surfactant in such formulations ranges from about 5 to about 15% by weight. The surfactant can be a single surfactant having the above-identified HLB or a mixture of two or more components having the desired HLB. Illustrative of surfactants useful in parenteral formulations are the class of polyoxyethylene sorbitan fatty acid esters, as for example, sorbitan monooleate, and the high molecular weight adducts of ethylene oxide with a hydrophobic base formed by the condensation of propylene oxide with propylene glycol. The concentration of active ingredient contained in these various parenteral dosage unit forms varies over a broad range and comprises from about 0.05 to about 20% by weight of the total formulation, the remaining component or components consisting of those liquid pharmaceutical excipients previously mentioned.

Milk and milk solids are a valuable adjunctive therapy in the treatment of peptic ulcers, and the compositions of this invention include liquid and solid compositions based on milk and milk solids. The compounds of the present invention or the compositions thereof can, if desired, be associated with other compatable pharmacologically active ingredients. Thus, for example, antacids and acid adsorbents such as aluminum hydroxide and magnesium trisilicate may also be included in compositions for oral administration in order to provide an immediate antacid effect. Other pharmacologically active ingredients that may be associated with the compounds of this invention include compounds affecting the central nervous system, as for example, long and short acting sedatives, such as barbiturates, antihistamimic agents, antiemetic agents such as cyclizine and diphenhydramine and anticholinergic agents such as atropine.

The invention described herein is more particularly illustrated by means of the following specific examples.

EXAMPLE 1

4-Amino-5-methyl-4H-1,2,4-triazole-3-thiol

Thiocarbohydrazide, 50 grams, is added to 600 ml. of acetic acid and heated to its reflux temperature for 30–45 minutes in an open flask. The solvent is evaporated until white crystals appear. The reaction mixture is heated to boiling to effect solution, and allowed to crystallize on cooling. The triazole so formed is collected by filtration, washed with water and dried at 60° C. in a vacuum oven to yield a compound having a m.p. 209°–11° C. (dec.).

Following essentially the same procedure, but substituting formic acid, hexanoic acid, trifluoroacetic acid, cyclohexyl carboxylic acid, ethoxymethylacetic acid and phenoxypropylacetic acid for the acetic acid above results in the preparation of the following triazoles:
4-amino-4H-1,2,4-triazole-3-thiol,
4-amino-5-hexyl-4H-1,2,4-triazole-3-thiol,
4-amino-5-trifluoro-4H-1,2,4-triazole-3-thiol,
4-amino-5-cyclohexyl-4H-1,2,4-triazole-3-thiol,
4-amino-5-ethoxymethyl-4H-1,2,4-triazole-3-thiol, and
4-amino-5-phenoxypropyl-4H-1,2,4-triazole-3-thiol, respectively.

EXAMPLE 2

4-Amino-5-phenyl-4H-1,2,4-triazole-3-thiol

Benzoylhydrazide, 30.0 grams, is suspended in 90 ml. of ethanol to which is added 22.3 grams of carbon disulfide and a solution of 15 grams of potassium hydroxide in 20 ml. of water with stirring and cooling. After 30 minutes of stirring the reaction mixture solidifies and 19 ml. of water is added. Methyl iodide, 33.0 grams, is added via dropwise addition with continued stirring. After approximately 10 minutes the methyl ester crystallizes and is precipitated by the addition of 200 ml. of water. The crude methyl 2-benzoyldithiocarbazinate is removed by filtration and recrystallized from ethanol to yield 17 grams of a compound having a m.p. of 167°–8° C.

An 85% solution of hydrazine hydrate, 20 ml., methyl 2-benzoyldithiocarbazinate, 20 grams, and 80 ml. of ethanol are refluxed with stirring for a period of 4 hours. Upon cooling 200 ml. of water are added followed by 50 ml. of concentrated hydrochloric acid. The desired 4-amino-5-phenyl-4H-1,2,4-triazole-3-thiol is removed by filtration and recrystallized from a 50% aqueous ethanol solution to yield a compound having a m.p. of 200°–1° C.

EXAMPLE 3

2-Bromo-3-methylcyclohexanone

3-Methylcyclohexanone, 22.4 grams, contained in 250 ml. of chloroform and 50 ml. of ethyl acetate, is heated to boiling. A mixture of 98.3 grams of cupric bromide and 50 ml. of ethyl acetate is added and heated to maintain elimination of hydrogen bromide. When all of the hydrogen bromide is evolved, the mixture is heated to its reflux temperature for 15 minutes, filtered and the filtrate evaporated to a small volume. The residue is placed upon an alumina column and eluted with methylene chloride. Evaporation of the eluate yields 35.5 grams of crude 2-bromo-3-methylcyclohexanone suitable for condensation with the triazoles of Examples 1 or 2.

Following essentially the same procedure, but substituting
3-propylcyclopentanone,
5-methylcyclopentanone,
4-methylcyclohexanone,
5-ethylcycloheptanone,
4-ethylcyclooctanone,
cyclooctanone,
3-butylcyclodecanone,
cyclododecanone, and
3-methylcyclododecanone
for the 3-methylcyclohexanone above results in the formation of
2-bromo-3-propylcyclopentanone,
2-bromo-5-methylcyclopentanone,
2-bromo-4-methylcyclohexanone,
2-bromo-5-ethylcycloheptanone,
2-bromo-4-ethylcyclooctanone,
2-bromocyclooctanone,
2-bromo-3-butylcyclodecanone,
2-bromocyclododecanone, and
2-bromo-3-methylcyclodocecanone, respectively

EXAMPLE 4

4-t-Butyl-2-chlorocyclohexanone

The compound 4-t-butylcyclohexanone, 154.3 grams, is dissolved in one liter of benzene to which a trace of ferric chloride is added. The mixture is heated and 148.5 grams of sulfuryl chloride is added dropwise in periodic increments. The reaction mixture is slowly heated to its reflux temperature and maintained at that temperature until no further evolution of hydrochloric acid is observed. The solvent is removed in vacuo and the residue dissolved in a small amount of heptane. The solution is passed through an alumina column and the eluate removed by evaporation under reduced pressure to yield 167.6 grams of crude 4-t-butyl-2-chlorocyclohexanone.

Following essentially the same procedure but substituting
3-butylcyclopentanone,
4-propylcyclohexanone,
3-ethylcyclohexanone,
4-isopropylcycloheptanone,
3-ethylcycloheptanone,
5-ethylcyclooctanone,
3-t-butylcyclooctanone,
5-isobutylcyclononanone, and
3-ethylcycloundecanone
for the 4-t-butylcyclohexanone above results in the formation of
3-butyl-2-chlorocyclopentanone,
2-chloro-4-propylcyclohexanone,
2-chloro-3-ethylcyclohexanone,
2-chloro-4-isopropylcycloheptanone,
2-chloro-3-ethylcycloheptanone,
2-chloro-5-ethylcyclooctanone,
3-t-butyl-2-chloro-cyclooctanone,
2-chloro-5-isobutylcyclononanone, and
2-chloro-3-ethylcycloundecanone, respectively.

Refluxing the 2-chlorocycloalkanones so obtained with a solution of sodium iodide in acetone results in the formation of the corresponding 2-iodocycloalkanones.

EXAMPLE 5

3-Ethyl-6,7,8,8a-tetrahydro-s-triazolo[3,4-b][1,3,4]cyclopentathiadiazine

The compounds 2-chlorocyclopentanone, 17.8 grams, 4-amino-5-ethyl-4H-1,2,4-triazole-3-thiol, 21.6 grams, and 250 ml. of absolute ethanol are refluxed for a period of approximately 3.5 hours. A few ml. of methanolic hydrogen chloride are added and the reaction mixture is evaporated to dryness. The residue is dissolved in dilute hydrochloric acid and extracted with ether. The aqueous solution is made alkaline with a dilute aqueous solution of sodium hydroxide and twice extracted with methylene chloride. The methylene chloride extracts are combined, dried over anhydrous magnesium sulfate, filtered and evaporated to dryness. The crude 3-ethyl-6,7,8,8a-tetrahydro-s-triazolo[3,4-b][1,3,4]-cyclopentathiadiazine so obtained is recrystallized twice from pentane to yield 16.4 grams of a product, m.p. 83°–5° C.

Following essentially the same procedure but substituting the various 4-amino-4H-1,2,4-triazole-3-thiols of Examples 1 and 2 and the various 2-chlorocycloalkanones of Example 4 for the 4-amino-5-ethyl-4H-1,2,4-triazole-3-thiol and 2-chlorocyclopentanone above results in the preparation of the corresponding s-triazolo[3,4-b][1,3,4]cycloalkathiadiazines.

EXAMPLE 6

6,7,8,9,10,10a-Hexahydro-3-methyl-s-triazolo[3,4-b][1,3,4]cycloheptathiadiazine hydrochloride The compounds 4-amino-5-methyl-4H-1,2,4-triazole-3-thiol, 26.0 grams, 2-chlorocycloheptanone, 31.0 grams, and absolute ethanol, 500 ml., are stirred at their reflux temperature for a period of approximately 4 hours under anhydrous conditions (the reflux condenser is equipped with a calcium chloride drying tube), whereupon the reaction mixture is concentrated in vacuo to a dark oil. The oil is dissolved in 100 ml. of methanol and ethyl acetate, 600 ml., added to induce the desired compound to crystallize. Recrystallization of the crude product from a solution of methanolethyl acetate results in the preparation of 22.6 grams of 6,7,8,9,10,10a-hexahydro-3-methyl-s-triazolo[3,4-b][1,3,4]cycloheptathiadiazine hydrochloride having a m.p. of 170°–1° C.

Following eesentially the same procedure but substituting
 4-amino-4H-1,2,4-triazole-3-thiol,
 4-amino-5-ethyl-4H-1,2,4-triazole-3-thiol,
 4-amino-5-propyl-4H-1,2,4-triazole-3-thiol,
 4-amino-5-heptyl-4H-1,2,4-triazole-3-thiol,
 4-amino-5-phenoxymethyl-4H-1,2,4-triazole-3-thiol, and
 4-amino-5-trifluoromethyl-4H-1,2,4-triazole-3-thiol
for the 4-amino-5-methyl-4H-1,2,4-triazole-3-thiol above results in the formation of the following hydrochloride salts, respectively:
 6,7,8,9,10,10a-hexahydro-s-triazolo[3,4-b][1,3,4]cycloheptathiadiazine (m.p. 173°–4° C.),
 3-ethyl-6,7,8,9,10,10a-hexahydro-s-triazolo[3,4-b][1,3,4]-cycloheptathiadiazine (m.p. 143°–4° C.),
 6,7,8,9,10,10a-hexahydro-3-propyl-s-triazolo[3,4-b][1,3,4]-cycloheptathiadiazine (m.p. 123°–4° C.),
 3-heptyl-6,7,8,9,10,10a-hexahydro-s-triazolo[3,4-b][1,3,4]-cycloheptathiadiazine (m.p. 96°–7° C.),
 6,7,8,9,10,10a-hexahydro-3-phenoxymethyl-s-triazolo[3,4-b]-[1,3,4]cycloheptathiadiazine (m.p. 155°–7° C.), and
 6,7,8,9,10,10a-hexahydro-3-trifluoromethyl-s-triazolo[3,4-b]-[1,3,4]cycloheptathiadiazine, respectively.

EXAMPLE 7

7,8,9,9a-Tetrahydro-3-methoxymethyl-6H-s-triazolo[3,4-b][1,3,4]cyclohexathiadiazine The compounds 4-amino-5-methoxymethyl-4H-1,2,4-triazole3-thiol, 32.0 grams, 2-chlorocyclohexanone, 28.0 grams, and absolute ethanol, 600 ml., are refluxed for about 4 hours. The reaction mixture is concentrated in vacuo to a brown oil. This oil is dissolved in 400 ml. of methylene chloride, extracted with two portions of 100 ml. each of a 10% aqueous NaOH solution, washed with a saturated NaCl solution, dried over anhydrous MgSO$_4$ and evaporated to an oily residue.

The addition of 100 ml. of a saturated NaCl solution results in the formation of crude oily crystals of the desired product, which are washed and triturated with ether to yield 31.0 grams of 7,8,9,9a-tetrahydro-3-methoxymethyl-6H-s-triazolo[3,4-b][1,3,4]cyclohexathiadiazine. Recrystallization from a methylene chloride-hexane solution results in a m.p. of 62°–3° C.

Using essentially the same procedure, substituting
 4-amino-4H-1,2,4-triazole-3-thiol,
 4-amino-5-methyl-4H-1,2,4-triazole-3-thiol,
 4-amino-5-trifluoromethyl-4H-1,2,4-triazole-3-thiol,
 4-amino-5-ethyl-4H-1,2,4-triazole-3-thiol,
 4-amino-5-propyl-4H-1,2,4-triazole-3-thiol,
 4-amino-5-cyclopropyl-4H-1,2,4-triazole-3-thiol,
 4-amino-5-heptyl-4H-1,2,4-triazole-3-thiol,
 4-amino-5-tridecyl-4H-1,2,4-triazole-3-thiol,
 4-amino-5-ethoxymethyl-4H-1,2,4-triazole-3-thiol,
 4-amino-5-phenoxymethyl-4H-1,2,4-triazole-3-thiol,
 4-amino-5-ethoxyethyl-4H-1,2,4-triazole-3-thiol,
 4-amino-5-phenyl-4H-1,2,4-triazole-3-thiol, and
 4-amino-5-butyl-4H-1,2,4-triazole-3-thiol in lieu of the 4-amino-5-methoxymethyl-4H-1,2,4-triazole-3-thiol above results in the formation of the following compounds, respectively:
 7,8,9,9a-tetrahydro-6H-s-triazolo[3,4-b][1,3,4]cyclohexathiadiazine (m.p. 146°–7.5° C.),
 7,8,9,9a-tetrahydro-3-methyl-6H-s-triazolo[3,4-b][1,3,4]-cyclohexathiadiazine (m.p. 103°–4° C.),
 7,8,9,9a-tetrahydro-3-trifluoromethyl-6H-s-triazolo[3,4-b]-[1,3,4]cyclohexathiadiazine (m.p. 100°–1° C.),
 3-ethyl-7,8,9,9a-tetrahydro-6H-s-triazolo[3,4-b][1,3,4]-cyclohexathiadiazine (m.p. 69°–70° C.),
 7,8,9,9a-tetrahydro-3-propyl-6H-s-triazolo[3,4-b][1,3,4]-cyclohexathiadiazine (m.p. 73°–4° C.),
 3-cyclopropyl-7,8,9,9a-tetrahydro-6H-s-triazolo[3,4-b]-[1,3,4]cyclohexathiadiazine (m.p. 118°–9° C.),
 3-heptyl-7,8,9,9a-tetrahydro-6H-s-triazolo[3,4-b][1,3,4]-cyclohexathiadiazine (m.p. 66°–7° C.),
 7,8,9,9a-tetrahydro-3-tridecyl-6H-s-triazolo[3,4-b][1,3,4]-cyclohexathiadiazine (m.p. 84°–5° C.),
 7,8,9,9a-tetrahydro-3-ethoxymethyl-6H-s-triazolo[3,4-b]-[1,3,4]cyclohexathiadiazine (m.p. 78.5°–9° C.),
 7,8,9,9a-tetrahydro-3-phenoxymethyl-6H-s-triazolo[3,4-b]-[1,3,4]cyclohexathiadiazine (m.p. 116°–7° C.),
 3-ethoxyethyl-7,8,9,9a-tetrahydro-6H-s-triazolo[3,4-b]-[1,3,4]cyclohexathiadiazine (m.p. 78°–9° C.),
 7,8,9,9a-tetrahydro-3-phenyl-6H-s-triazolo[3,4-b][1,3,4]-cyclohexathiadiazine (m.p. 187°–8° C.), and
 3-butyl-7,8,9,9a-tetrahydro-6H-s-triazolo[3,4-b][1,3,4]-cyclohexathiadiazine as the free base compounds, respectively.

Substituting 4-amino-5-ethyl-4H-1,2,4-triazole-3-thiol for the 4-amino-5-methoxymethyl-4H-1,2,4-triazole-3-thiol above and 2-chloro-4-ethylcyclohexanone and 4-t-butyl-2-chlorocyclohexanone for the 2-chlorocyclohexanone above results in the preparation of 3,8-diethyl-7,8,9,9a-tetrahydro-6H-s-triazolo[3,4-b][1,3,4]-cyclohexathiadiazine (m.p. 76°–9° C.), and 8-t-butyl-3-ethyl-7,8,9,9a-tetrahydro-6H-s-triazolo[3,4-b]-[1,3,4]cyclohexathiadiazine (m.p. 130°–2° C.), respectively.

Substituting 4-amino-5-methyl-4H-1,2,4-triazole-3-thiol and 2-chloro-3-methylcyclohexanone for the 4-amino-5-methoxymethyl-4H-1,2,4-triazole-3-thiol and 2-chlorocyclohexanone above results in the preparation of 7,8,9,9a-tetrahydro3,7-dimethyl-6H-s-triazolo[3,4-b][1,3,4]cyclohexathiadiazine having a m.p. of 124°–7° C.

The corresponding 2-chlorocycloheptanones and 2-chlorocyclooctanones can be substituted for the various 2-chlorocyclohexanones of this Example to prepare the analogous substituted 6,7,8,9,10,10a-hexahydro-s-triazolo[3,4-b][1,3,4]cycloheptathiadiazines and 7,8,9,10,11,11a-hexahydro6H-s-trizolo[3,4-b][1,3,4]cyclooctathiadiazines.

EXAMPLE 8

7,8,9,10,11,11a-Hexahydro-3-methyl-6H-s-triazolo [3,4-b][1,3,4]cyclooctathiadiazine hydrochloride The compounds, 4-amino-5-methyl-4H-1,2,4-triazole-3-thiol, 78 grams, 2-chlorocyclooctanone, 10.0 grams, and 300 ml. of absolute ethanol are stirred at the reflux temperature for a period of about 4 hours. The solvent is removed in vacuo and the residue crystallized from a methanolethyl acetate mixture to yield approximately 9.3 grams of 7,8,9,10,11,11a-hexahydro-3-methyl-6H-s-triazolo[3,4-b][1,3,4]-cyclooctathiadiazine hydrochloride having a melting point of 187°–9° C.

Following essentially the same procedure and substituting 4-amino-5-ethyl-4H-1,2,4-triazole-3-thiol,
4-amino-5-propyl-4H-1,2,4-triazole-3-thiol,
4-amino-5-heptyl-4H-1,2,4-triazole-3-thiol, and
4-amino-5-ethoxymethyl-4H-1,2,4-triazole-3-thiol for the 4-amino-5-methyl-4H-1,2,4-triazole-3-thiol above results in the preparation of 3-ethyl-7,8,9,10,11,a-hexahydro-6H-s-triazolo[3,4-b][1,3,4]-cyclooctathiadiazine (m.p. 94°–5° C.) as the free base, 7,8,9.10,11,11a-hexahydro-3-propyl-6H-s-triazolo[3,4-b][1,3,4]-cyclooctathiadiazine as the hydrochloride salt (m.p. 144°–5° C.), 3-heptyl-7,8,9,10,11,11a-hexahydro-6H-s-triazolo[3,4-b]-[1,3,4]cyclooctathiadiazine as the hydrochloride salt (m.p. 119°–20° C.), and 3-ethoxymethyl-7,8,9,10,11,11a-hexahydro-6H-s-triazolo-[3,4-b][1,3,4]cyclooctathiadiazine (m.p. 93°–4° C.) as the free base, respectively.

EXAMPLE 9

7,8,9,10,11,12,13,14,15,15a-Decahydro-3-methyl-6H-s-triazolo [3,4-b][1,3,4]cyclododecathiadiazine The compounds, 4-amino-5-methyl-4H-1,2,4-triazole-3-thiol, 21.0 grams, 2- bromocyclododecanone, 40.0 grams, and 400 ml. of absolute ethanol are stirred at the reflux temperature for about 4 hours. The solvent is removed in vacuo and the residue is dissolved in 250 ml. of methylene chloride. The organic solution is extracted twice with 100 ml. portions of an aqueous 10% NaOH solution, followed by 200 ml. of an aqueous saturated NaCl solution, dried over anhydrous MgSO₄, concentrated to approximately 100 ml. and hexane added to form a yellow powder. Recrystallization from a methylene chloride-hexane solution yields 7,8,9,10,11,12,13,14,15,15a-decahydro-3-methyl 6H-s-triazolo[3,4-b][1,3,4]cyclododecathiadiazine having a m.p. of 138°–9° C.

Following essentially the same procedure but subsituting 4-amino-5-ethyl-4H-1,2,4-triazole-3-thiol for the 4-amino-5-methyl-4H-1,2,4-triazole-3-thiol above, results in the preparation of 7,8,9,10.11,12,13,14,15,15a-decahydro-3-ethyl-6H-s-triazolo[3,4-b][1,3,4]cyclododecathiadiazine as the hydrochloride salt having a m.p. of 155°–7° C.

EXAMPLE 10

5a,6,7,8,9,9a-Hexahydro-5H-s-triazolo[3,4-b][1,3,4]cyclohexathiadiazine

Sodium borohydride, 10.1 grams (0.3 mole), is added in increments to 500 milliliters of isopropanol containing 20.4 grams (0.084 mole) of 7,8,9,9a-tetrahydro-6H-s-triazolo [3,4-b][1,3,4]cyclohexathiadiazine. The reaction mixture is maintained at its reflux temperature for about 17 hours, 200 milliliters of methanol are added and the mixture refluxed for an additional 2 hours. The solvents are removed in vacuo, the semi-solid residue is acidified with a solution of 25 milliliters of acetic acid in 200 milliliters of water, and the mixture extracted with methylene chloride. The combined methylene chloride extracts are dried over anhydrous magnesium sulfate, filtered, concentrated in vacuo and recrystallized from methanol to yield 3.5 grams of 5a, 6,7,8,9,9a-hexahydro-5H-s-triazolo[3,4-b][1,3,4]cyclohexathiadiazine, having a m.p. of 238°–40° C.

Following essentially the same procedure but substituting:

6,7,8,9.10,10a-hexahydro-3-phenoxymethyl-s-triazolo[3,4-b]-[1,3,4]cycloheptathiadiazine, and
3-ethyl-6,7,8,8a-tetrahydro-6H-s-triazolo[3,4-b]1,3,4]cyclopentathiadiazine, for the 7,8,9,9a-tetrahydro-6H-s-triazolo[3,4b][1,3,4]-cyclohexathiadiazine above results in the preparation of the following compounds:

5,5a,6,7,8,9,10,10a-octahydro-3-phenoxymethyl-s-triazolo[1,3-b]-[1,3,4]cycloheptathiadiazine (m.p. 131.5°–2.5° C.) and 3-ethyl-5,5a,5,7,8,8a-hexahydro-s-triazolo[3,4-b][1,3,4]-cyclopentathiadiazine (m.p. 92°–4° C.), respectively.

Following essentially the same procedure, the following compounds are substituted for the 7,8,9,9a-tetrahydro-6H-s-triazolo[3,4-b][1,3,4]cyclohexathiadiazine above:

7,8,9,9a-tetrahydro-3-methoxymethyl-6H-s-triazolo[3,4-b]-[1,3,4]cyclohexathiadiazine,
3-ethyl-7,8,9,9a-tetrahydro-6H-s-triazolo[3,4-b][1,3,4]-cyclohexathiadiazine,
3-ethyl-6,7,8,9,10,10a-hexahydro-s-triazolo[3,4-b][1,3,4]-cycloheptathiadiazine,
3-ethyl-7,8,9,10,11,11a-hexahydro-6H-s-triazolo[3,4-b][1,3,4]-cyclooctathiadiazine,
6,7,8,9,10,10a-hexahydro-3-methyl-s-triazolo[3,4-b][1,3,4]-cycloheptathiadiazine, and
7,8,9,9a-tetrahydro-3-phenyl-6H-s-triazolo[3,4-b][1,3,4]-cyclohexathiadiazine.

The following products are obtained as their hydrochloride salts, respectively, when recrystallized from diethyl ether/tetrahydrofuran, methanol/ethyl acetate or chloroform/methanol solvent mixtures, that have been saturated with dry hydrogen chloride:

5a,6,7,8,9,9a-hexahydro-3-methoxymethyl-5H-s-triazolo[3,4b]-[1,3,4]cyclohexathiadiazine hydrochloride (m.p. 151.5°–2.5° C.), 3-ethyl-5a,6,7,8,9,9a-hexahydro-5H-s-triazolo[3,4-b][1,3,4]-cyclohexathiadiazine hydrochloride (m.p. 168°–9° C.), 3-ethyl-5,5a,6,7,8,9,10,10a-octahydro-s-triazolo[3,4-b]-[1,3,4]cycloheptathiadiazine hydrochloride (m.p. 172°–5° C.), 3-ethyl-5a,6,7,8,9,10,11,11a-octahydro-5H-s-triazolo[3,4-b]-[1,3,4]cyclooctathiadiazine hydrochloride (m.p. 174°–6° C.), 5,5a,6,7,8,9,10,10a-octahydro-3-methyl-s-triazolo[3,4-b]-[1,3,4]cycloheptathiadiazine hydrochloride (m.p. 193°–4° C.), and 5a,6,7,8,9,9a-hexahydro-3-phenyl-5H-s-triazolo[3,4-b][1,3,4]-cyclohexathiadiazine hydrochloride (m.p. 205°–7° C.).

EXAMPLE 11

5a,6,7,8,9,9a-Hexahydro-3-methoxymethyl-5H-s-triazolo[3,4-b][1,3,4]cyclohexathiadiazine hydrochloride Lithium aluminum hydride, 1.44 grams, is suspended in 50 milliliters of dry tetrahydrofuran and added via dropwise addition to a stirred solution of 10.4 grams of 7,8,9,9a-tetrahydro-3-methoxymethyl-6H-s-triazolo[3,4-b][1,3,4]cyclohexathiadiazine dissolved in tetrahydrofuran. The reaction mixture is stirred for approximately 3 hours at room temperature and the excess lithium aluminum hydride decomposed via the dropwise addition of water (100 ml.). The resulting reaction mixture is extracted with methylene chloride and the combined extracts are extracted with a 10% solution of hydrochloric acid. The hydrochloric acid extract is neutralized with diilute base and the resulting oil which forms is extracted into methylene chloride. The combined methylene chloride extracts are evaporated to dryness and the residue is crystallized from a diethyl ether/tetrahydrofuran mixture to which ethereal hydrogen chloride has been added to yield 1.8 grams of 5a,6,7,8,9,9a-hexahydro-3-methoxymethyl-5H-s-triazolo[3,4-b][1,3,4]cyclohexathiadiazine hydrochloride having a m.p. of 151.5°–2.5° C.

EXAMPLE 12

5-Acetyl-3-ethyl-5,5a,6,7,8,9,10,10a-octahydro-s-triazolo[3,4b][1,3,4]cycloheptathiadiazine The compound 3-ethyl-5,5a,6,7,8,9,10,10a-octahydro-s-triazolo[3,4-b][1,3e,4]cycloheptathiadiazine hydrochloride, 25.0 grams (0.09 mole) is stirred with methylene chloride and 5% aqueous sodium hydroxide solution. The methylene chloride layer is separated, dried over anhydrous magnesium sulfate and concentrated to a yellow oil. To this oil is added 125 milliliters of acetic anhydride and 10.0 grams of sodium acetate. The resulting suspension is stirred and heated at its reflux temperature for approximately 20 hours. The reaction mixture is concentrated in vacuo to yield a brown semi-solid which is dissolved in a 2-phase system of water and methylene chloride. The methylene chloride solution is separated, washed with water, dried over anhydrous magnesium sulfate, filtered and concentrated in vacuo to yield 23.8 grams of crude 5-acetyl-3-ethyl-5,5a,6,7,8,9,10,10a-octahydro-s-triazolo[3,4-b][1,3,4]cycloheptathiadiazine. Recrystallization from a solution of methylene chloride and heptane, followed by a second recrystallization from ethyl acetate, yields the desired product having a m.p. of 130°–1° C.

EXAMPLE 13

5-[N-Carbamoylacetic acid (ethyl ester)]-5a,6,7,8,9,9a-hexahydro-5H-s-triazolo[3,4b][1,3,4]-cyclohexathiadiazine The compound 5a,6,7,8,9,9a-hexahydro-5H-s-triazolo-[3,4-b][1,3,4]cyclohexathiadiazine, 12.6 grams (0.057 mole), and carbethoxymethylisocyanate, 13.0 milliliters, are heated with stirring at steam bath temperature. Upon cooling, the reaction mixture solidifies and the solid so obtained is washed with hexane, followed by a wash with cold aqueous 15% ethanol. The light tan solid so obtained is recrystallized from a 40% ethanol/water mixture to yield 10.0 grams of 5-[N-carbamoylacetic acid (ethyl ester)]-5a,6,7,8,9,9a-hexahydro-5H-s-triazolo[3,4-b][1,3,4]cyclohexathiadiazine having a m.p. of 164°–1.5° C.

EXAMPLE 14

5-Cinnamoyl-3-ethyl-5a,6,7,8,9,9a-hexahydro-5H-s-triazolo[3,4b][1,3,4]cyclohexathiadiazine A solution of 3-ethyl-5a,6,7,8,9,9a-hexahydro-5H-s-triazolo[3,4-b][1,3,4]cyclohexathiadiazine, 4.0 grams (0.0115 mole), cinnamoyl chloride, 2,6 grams (0.0156 mole), 45 milliliters of pyridine and 40 milliliters of dry benzene are heated with stirring at the reflux temperature for approximately 30 minutes. Dilution of the reaction mixture with hexane on cooling yields a tan semi-solid. This semi-solid is crystallized from a mixture of methanol/water to yield 0.45 grams of 5-cinnamoyl-3-ethyl-5a,5,7,8,9,9a-hexahydro-5H-s-triazolo[3,4-b][1,3,4]cyclohexathiadiazine as yellow needles having a m.p. of 140°–1° C.

EXAMPLE 15

5-Anilinocarbonyl-5,5a,6,7,8,9,10,10a-octahydro-3-methyl-s-triazolo[3,4-b][1,3,4]cycloheptathiadiazine A solution of 5.0 grams of 5,5a,6,7,8,9,10,10a-octahydro-3-methyl-s-triazolo[3,4-b][1,3,4]cycloheptathiadiazine (0.022 mole) and an excess of phenylisocyanate dissolved in 200 milliliters of benzene are heated with stirring at the reflux temperature for approximately 45 minutes. The desired 5-anilinocarbonyl-5,5a,6,7,8,9,10,10a-octahydro-3-methyl-s-triazolo[3,4-b][1,3,4]cycloheptathiadiazine appears as a white precipitate, which when filtered and recrystallized twice from methanol yields 2.9 grams of crystalline product having a m.p. of 213°–5° C.

EXAMPLE 16

Antisecretory Activity

Male Sprague-Dawley rats weighing 200-250 grams each are fasted 48 hours prior to testing. Water is given ad lib for the first 24 hour period after which the water is replaced with an aqueous 10% dextrose and 0.5% sodium chloride solution. Six rats per compound group are treated as follows.

Under light anesthesia, a ventral midline incision approximately 10 mm. in length is made below the sternum. The duodenal bulb is revealed and the pyloric sphincter is tightly ligated with surgical silk being careful to avoid rupturing the surrounding blood vessels.

The compound to be tested, 3-ethyl-5a,6,7,8,9,10,11,11a-octahydro-5H-s-triazolo[3,4-b][1,3,4]cyclooctathiadiazine, is administered as the hydrochloride salt by injection into the duodenum at a point distal to the ligature at a dosage of 25 mg/kg of body weight in an aqueous suspension of 0.1 ml/100 grams of body weight, said suspension containing 0.5% of hydroxyethylcellulose as a suspending agent. Four milliliters of water are injected into the stomach near the pyloric sphincter to provide a uniform amount of stomach distension in order to trigger gastric flow. The incisions are closed and the rats are injected i.p. with 2 ml. of physiological saline to restore fluid loss which occurs during surgery.

Following a four hour recovery period, the rats are sacrificed and their stomach contents harvested. The stomach contents are centrifuged at 1500 r.p.m. for 10 minutes and the volume and pH recorded. Control groups containing a mean volume of less than 8.0 ml. indicate an invalid test. The gastric contents of both control and test groups of animals are titrated against a standard solution of 0.1N sodium hydroxide.

Utilizing this procedure in two separate experiments, the compound, 3-ethyl-5a,6,7,8,9,10,11,11a-octahydro-5H-s-triazolo[3,4-b][1,3,4]cyclooctathiadiazine exhibits a reduction of 58 and 60% of total gastric acidity when compared to the control animals.

EXAMPLE 17

Tablet Formulation

An illustrative preparation for tablets is as follows:

| | Ingredients | Per Tablet |
|---|---|---|
| (a) | 3-ethyl-5a,6,7,8,9,10,11,11a-octahydro-5H-s-triazolo[3,4-b][1,3,4]cyclooctathiadiazine | 150 mg. |
| (b) | Wheat starch and granulated starch paste (10% w/v) | 15 mg. |
| (c) | Lactose | 33.5 mg. |
| (d) | Magnesium stearate | 1.5 mg. |

The granulation obtained upon mixing lactose, starch and granulated starch paste is dried, screened and mixed with the active ingredient and magnesium stearate. The mixture is compressed into tablets weighing 200 mg. each.

EXAMPLE 18

Capsule Preparation

An illustrative preparation for hard gelatin capsules is as follows:

| | Ingredients | Per Capsule |
|---|---|---|
| (a) | 5a,6,7,8,9,9a-hexahydro-3-methoxymethyl-5H-s-triazolo[3,4-b][1,3,4]cyclohexathiadiazine hydrochloride | 200 mg. |
| (b) | Talc | 35 mg. |

The formulation is prepared by passing the dry powders of both (a) and (b) through a fine mesh screen and mixing them well. The mixed powders are then filled into No. 0 hard gelatin capsules at a net fill of 235 mg. per capsule.

Soft gelatin capsules can be prepared in a similar fashion. Alternatively, the talc may be omitted and the active ingredient filled directly as a granulation, slug or compressed tablet into the rotary die or plate mold in which the soft gelatin capsule is to be formed.

EXAMPLE 19

Preparation of a Parenteral Formulation

An illustrative composition for a parenteral injection is the following emulsion:

| Each ml. Contains | Ingredients | Amount |
|---|---|---|
| 50 mg. | 5,5a,6,7,8,9,10,10a-octahydro-3-methyl-s-triazolo[3,4-b][1,3,4]cycloheptathiadiazine hydrochloride | 1.0 g. |
| 100 mg. | Polyoxyethylene sorbitan monooleate | 2.0 g. |
| 0.0064 g. | Sodium chloride | 0.128 g. |
| | Water for injection, q.s. | 20 ml. |

The parenteral composition is prepared by dissolving 0.64 g. of sodium chloride in 100 ml. of water for injection, mixing the polyoxyethylene sorbitan monooleate with the 5,5a,6,7,8,9,10,10a-octahydro-3-methyl-s-triazolo[3,4-b][1,3,4]cycloheptathiadiazine hydrochloride, adding a sufficient solution of the sodium chloride in water to the active ingredient and polyoxyethylene sorbitan monooleate to bring the volume to 20 ml., shaking the mixture, and finally autoclaving the mixture for 20 minutes at 110 C., at 15 p.s.i.g. steam pressure. The composition can be dispensed either in a single ampule for subsequent use in multiple dosages or in groups of 10 and 20 ampules for a single dosage administration.

EXAMPLE 20

Preparation of an Oral Syrup

A two percent weight per volume of syrup containing 3-ethyl-5,5a,6,7,8,8a-hexahydro-s-triazolo[3,4b][1,3,4] cyclopentathiadiazine is prepared by the usual pharmaceutical techniques in accordance with the following formula:

| | Ingredients | Grams |
|---|---|---|
| (a) | 3-ethyl-5,5a,6,7,8,8a-hexahydro-s-triazolo[3,4-b][1,3,4]cyclopentathiadiazine | 2.0 |
| (b) | Sucrose | 33.0 |
| (c) | Chloroform | 0.25 |
| (d) | Sodium benzoate | 0.4 |
| (e) | Methyl p-hydroxybenzoate | 0.02 |
| (f) | Vanillin | 0.04 |
| (g) | Glycerol | 1.5 |
| (h) | Purified water to 100.0 ml. | |

We claim:

1. A triazolocycloalkylhydrothiadiazine having the formula:

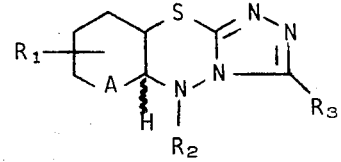

wherein

R₁ is selected from the group consisting of hydrogen and lower alkyl having from 1 to 4 carbon atoms;

R₂ is selected from the group consisting of hydrogen, acetyl, N-carbamoylacetic acid (ethyl ester), cinnamoyl and anilinocarbonyl;

R₃ is selected from the group consisting of hydrogen, alkyl having from 1 to 15 carbon atoms, trifluoromethyl, cycloalkyl having from 3 to 6 carbon atoms, phenyl, alkoxyalkyl having from 2 to 8 carbon atoms and phenoxyalkyl having from 7 to 10 carbon atoms;

A is a sigma bond or the radical —(CH₂)ₙ— in which n is a whole integer of from 1 to 7, and the pharmaceutically acceptable acid addition salts thereof.

2. A compound according to claim 1 wherein R₂ is hydrogen.

3. A compound according to claim 1 wherein A is the radical —(CH₂)ₙ— and n is the integer 1.

4. A compound according to claim 1 wherein a is the radical —(CH₂)ₙ— and n is the integer 2.

5. The compound 3-ethyl-5a,6,7,8,9,10,11,11a-octahydro-5H-s-triazolo[3,4-b][1,3,4]cyclooctathiadiazine.

6. The compound 5-,6,7,8,9,10,11,11a-octahydro-3-methyl-s-triazolo[3,4-b][1,3,4]cycloheptathiadiazine.

7. The compound 5-a,6,7,8,9,9a-hexahydro-3-methoxymethyl-5H-s-triazolo[3,4-b][1,3,4]cyclohexathiadiazine.

8. A method of preparing a triazolocycloalkylhydrothiadiazine having the formula:

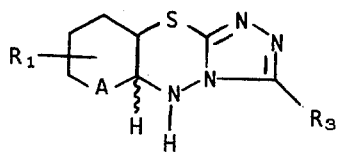

wherein R₁ is selected from the group consisting of hydrogen and lower alkyl having from 1 to 4 carbon atoms; R₃ is selected from the group consisting of hydrogen, alkyl having from 1 to 15 carbon atoms, trifluoromethyl, cycloalkyl having from 3 to 6 carbon atoms, phenyl alkoxyalkyl having from 2 to 8 carbon atoms and phenoxyalkyl having from 7 to 10 carbon atoms; A is a sigma bond or the radical —(CH₂)ₙ— in which n is a whole integer of from 1 to 7 or the pharmaceutically acceptable acid addition salts thereof; which comprises reducing in solution a triazolocycloalkylthiadiazine of the formula:

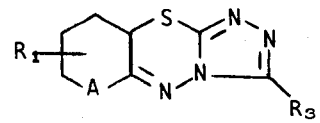

wherein R₁, R₃ and A are as defined above, with sodium borohydride or lithium aluminum hydride; and recovering the triazolocycloalkylhydrothiadiazine therefrom.

9. A method of reducing gastric secretion which comprises administering a therapeutically effective amount of a triazolocycloalkylhydrothiadiazine of claim 1 to mammals in need thereof.

10. A method according to claim 9 in which the triazolocycloalkylhydrothiadiazine is administered in an amount of from 1 to 200 milligrams per kilogram of body weight per day.

11. A therapeutic composition in dosage unit form comprising from 5 milligrams to 2.0 grams of a compound of claim 1 and a pharmaceutical carrier.

* * * * *

UNITED STATES PATENT AND TRADEMARK OFFICE
CERTIFICATE OF CORRECTION

PATENT NO. : 3,954,981
DATED : May 4, 1976
INVENTOR(S) : William L. Albrecht and Winton D. Jones It is certified that error appears in the above-identified patent and that said Letters Patent are hereby corrected as shown below:

Column 17, line 53, "[1,3e,4]" should read "[1,3,4]";
Column 18, line 22, "164°-1.5°C." should read "164-5.5°C.";
Column 18, line 29, "2,6 grams" should read "2.6 grams";
Column 21, line 24, "5-,6,7,8,9,10,11,11a-" should read "5,5a,6,7,8,9,10,10a-"; Column 22, line 7, "phenyl alkoxyalkyl" should read "phenyl, alkoxyalkyl".

Signed and Sealed this

Twenty-fifth Day of January 1977

[SEAL]

Attest:

RUTH C. MASON
*Attesting Officer*

C. MARSHALL DANN
*Commissioner of Patents and Trademarks*